United States Patent
Clausen et al.

[11] Patent Number: 6,099,804
[45] Date of Patent: *Aug. 8, 2000

[54] SENSOR AND MEMBRANE FOR A SENSOR

[75] Inventors: Lydia Dahl Clausen, Lynge; Allan Milton Byrnard, Copenhagen S; Jesper Svenning Kristensen, Lyngby, all of Denmark

[73] Assignee: Radiometer Medical A/S, Brønshøj, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/950,362

[22] Filed: Oct. 6, 1997

Related U.S. Application Data

[63] Continuation of application No. PCT/DK97/00111, Mar. 14, 1997.

[30] Foreign Application Priority Data

Mar. 29, 1996 [DK] Denmark ................................. 0360/96

[51] Int. Cl.[7] ................................................. G01N 27/00
[52] U.S. Cl. ................................. 422/82.01; 422/82.03; 204/403; 204/416; 210/490; 210/500.21; 210/500.24; 210/500.27; 210/500.36
[58] Field of Search ..................................... 204/194, 400, 204/403, 416; 435/287.9; 436/95; 422/82.01; 210/490, 500.21, 500.24, 500.27, 500.36

[56] References Cited

U.S. PATENT DOCUMENTS

| | | | |
|---|---|---|---|
| 4,840,636 | 6/1989 | Bauser et al. | 8/115.52 |
| 4,885,077 | 12/1989 | Karakelle et al. | 204/403 |
| 5,019,261 | 5/1991 | Stengaard | 210/490 |
| 5,543,465 | 8/1996 | Bell et al. | 525/182 |

FOREIGN PATENT DOCUMENTS

| | | | |
|---|---|---|---|
| 4002513 C1 | 7/1991 | Germany | C08J 5/12 |
| WO 92/04438 | 3/1992 | WIPO | C12M 1/40 |
| WO 96/17883 | 6/1996 | WIPO | C08J 5/22 |
| WO 96/18498 | 6/1996 | WIPO | B32B 5/16 |

OTHER PUBLICATIONS

W. Matuszewski et al, "Amperometric Glucose Biosensor for an Undiluted Whole–Blood Analysis", Anal. Sci., Jun. 1994 vol. 10, pp. 423–428.

*Primary Examiner*—David A. Redding
*Attorney, Agent, or Firm*—Mark E. Waddell; Stephen M. Haracz; Bryan Cave LLP

[57] ABSTRACT

In a sensor for measuring an analyte in a biological sample whose measuring surface is covered by or comprises a membrane, the membrane has free groups on the surface facing the sample. The surface is modified such that a hydrophilic component is immobilized on the surface in such a manner that chains of the hydrophilic component are chemically bonded to free groups on the surface. Thus, the surface is provided with a more hydrophilic character relative to its unmodified state.

26 Claims, 3 Drawing Sheets

SENSOR AND MEMBRANE FOR A SENSOR

This is a continuation of International Application No. PCT/DK97/00111.

The invention relates to a sensor for measuring an analyte in a biological sample having a measuring surface covered by or comprising a membrane through which the analyte to be measured penetrates towards the measuring surface, said membrane having free groups on the surface facing the sample.

One of the difficulties in selecting a membrane for a sensor to be used for measuring on whole blood is that some membrane materials have a surface character which tends to make some macromolecular elements of the blood, such as blood proteins and red blood cells, stick to the surface of the membrane. This results in a poor measurement quality of the sensor as reproducible measurement results are not obtainable when the measuring surface is coated. The tendency towards surface coating seems to depend on i.a. whether the membrane surface has a hydrophilic or hydrophobic character as a hydrophobic surface has a stronger tendency towards coating.

It has been attempted to solve the problem by making the membrane facing the sample or outer membrane of materials having minimal tendency towards coating. An analysis of different outer membranes applied in a biosensor for measuring glucose is disclosed in Matuszewski W, Trojanowicz M, Lewenstam A, Moszcyska and Lange-Moroz E. Amperometric glucose biosensor for an undiluted whole-blood analysis. Analytical Sciences 1994; Vol. 10: 423–428. The article discloses the application of e.g. polycarbonate, polyester, polyethylene terephthalate, polypropylene, etc.

According to the article, good results are obtained by using an outer membrane of polypropylene (PP) from Celanese. The surface character of said membrane is usually hydrophobic and consequently should not be very suitable as an outer membrane, cf. above. However, wetting the membrane with a hydrophilic component/surfactant provides a hydrophilic surface character, and good results have been obtained. The article discloses wetting with different hydrophilic components/surfactants. The best result was obtained by wetting a PP membrane with a surfactant designated Triton X-100.

The wetting process proper consisted in dipping the PP membrane into a solution of surfactant for 10 minutes, rinsing the membrane with distilled water followed by wiping the membrane.

Even after a number of measurements on whole blood, the outer membrane showed no signs of adsorbing red blood cells. Further, within a two-week period no significant change of the measuring signal occurred. In between the measurements the outer membrane was kept in a phosphate buffer solution at 4° C.

However, the sensor disclosed in the article has the disadvantage that it is not suitable in automatic analyzers such as the analyzer ABL™620 from Radiometer Medical A/S, Copenhagen, Denmark because the surface treatment of the outer membrane cannot stand the repeated rinse procedures which the analyzer performs automatically (more specifically an instrument-driven rinse procedure upon each measurement). These procedures are performed by means of special rinse solutions. The hydrophilic component/surfactant will be washed off and the outer membrane will gradually loose its hydrophilic character. This will result in coatings on the surface of the membrane causing poor reproducibility and/or decreasing measuring signals, cf. above.

Accordingly, the purpose of the invention is to provide a sensor with a membrane facing the sample which has no tendency towards coating and which is resistant to repeated rinse procedures.

This is obtained by the sensor according to the invention which is characterized in that the surface is modified such that a hydrophilic component is immobilised on the surface in such a manner that chains of the hydrophilic component are chemically bonded to free groups on the surface, thus providing the surface with a more hydrophilic character in relation to its unmodified state.

As the hydrophilic component is chemically bonded to the free groups on the surface of the membrane, the component is not leached out, even after repeated rinse procedures of the sensor. Further, the sensor requires no special storage in between the measurements as the membrane with the chemically bonded hydrophilic component is more stable than e.g. a membrane only wetted with a hydrophilic component.

The sensor according to the invention may be any sensor whose measuring surface is covered by or comprises a sample-contacting membrane. It is most likely that all sensors applied for measuring on biological samples may advantageously be embodied according to the invention. Examples of such sensors are gas sensors such as sensors for measurement of oxygen, carbon dioxide and ammonia; electrolyte sensors such as sensors for measurement of lithium, potassium, sodium, magnesium, calcium, ammonium, bicarbonate and chloride; biosensors such as enzyme sensors for measurement of glucose, cholesterol, lactate, creatinin, urea, carbamide, pyruvate, alcohol, bilirubin, ascorbate, phosphate, protein, triglycerides, phenylananine, tyrosin and hypoxanthine and immunosensors.

Sensors according to the invention may be based on any suitable measuring technique and may thus be based on e.g. electrochemical or optical principles.

The sensor according to the invention is primarily an electrochemical (amperometric) enzyme electrode having a two- or multi-layered membrane where the membrane layer facing the sample is porous. The porosity of the membrane layer facing the sample is primarily selected such that the membrane layer is a so-called substrate-limiting membrane layer as further disclosed in e.g. the specification of Danish Patent No. DK 170103.

In this context, a biological sample is a sample of whole blood, serum, plasma, or a sample of a body fluid in a natural or treated state.

The material for the membrane layer facing the sample (outer membrane layer) may be selected among all materials suitable for sensors and is most often a polymeric foil. The particular selection may take place in the light of requirements as to the permeability of certain agents, requirements as to resistance, strength, etc. It is merely required that the membrane has free groups on its surface to which the hydrophilic component may be bonded. Said free groups may be present in the natural state of the membrane or be applied by means of e.g. basic hydrolysis or plasma treatment.

Different rinse conditions may have an impact on the selection of a hydrophilic component. The hydrophilic component must be adapted so that sufficient washing from the pores of the membrane of e.g. the blood components, penetrating into the pores, may be obtained in between the measurements. Adaption of the molecular weight of the hydrophilic component to different rinse conditions of the analyzer may also be required in order to obtain sufficient washing of the pores in between the measurements.

A polyethylene glycol (PEG) of suitable chain length/ molecular weight and heparin are particularly preferred hydrophilic components which may be bonded to free groups of the membrane or membrane portion, e.g. free groups of carboxylic acid with a suitable coupling reagent. Other suitable hydrophilic components or surface modified agents may be selected among hydrophilic natural polymers having similar surface modifying properties as PEG, e.g. hyaluronic acid, phospholipides, agarose, chitosan, cyclodextrin, alginate, collagen, lignin, pectin and polysaccharides and celulose-based polymers such as dextrin, hydroxyalkyl celluloses, cellulose acetates, albumin, gelatin, agar, carageenans and starch; hydrophilic synthetic polymers having similar surface modifying properties as PEG, e.g. polyvinylalcohol/polyvinylacetates, polyvinyl pyrrolidone, hydroxymethylmethacrylate, hydroxyethylacrylate, acrylic acid, allyl alcohol and acrylic polymers (hydrogels); plasma polymerised polymers (acryls). Besides, reconcilability with the sensor is, of course, presumed.

It is important that the chains of the hydrophilic component are not so long that shear forces detach them from the surface of the membrane.

It is also important in connection with porous membranes or membrane layers that the chains of the hydrophilic component are not so long that they block the pores, thus preventing the analyte to permeate through the membrane or the membrane layer.

In this context, the unmodified state of the surface of the membrane is the state prior to modification with the hydrophilic component. This need not necessarily be the natural state in that some membranes, as mentioned above, may be subjected to basic hydrolysis or plasma treatment in order to apply free groups on the surface. In this case, the unmodified state is the state after application of the free groups, but prior to the modification with the hydrophilic component.

In a preferred embodiment, the membrane or membrane layer is porous and chains of the hydrophilic component are penetrated into the pores of the membrane and bonded to free groups of the surfaces of the pores. In this case, when selecting a hydrophilic component it is furthermore important to ensure that the chains are not so long that they cannot get into the pores of the membrane or membrane layer and when placed on the surfaces of the pores will not block the pores by reducing the open cross-sectional area of the pores too much.

BRIEF DESCRIPTION OF DRAWINGS

In the following the invention is further explained with reference to the drawing, in which.

Figure 1:
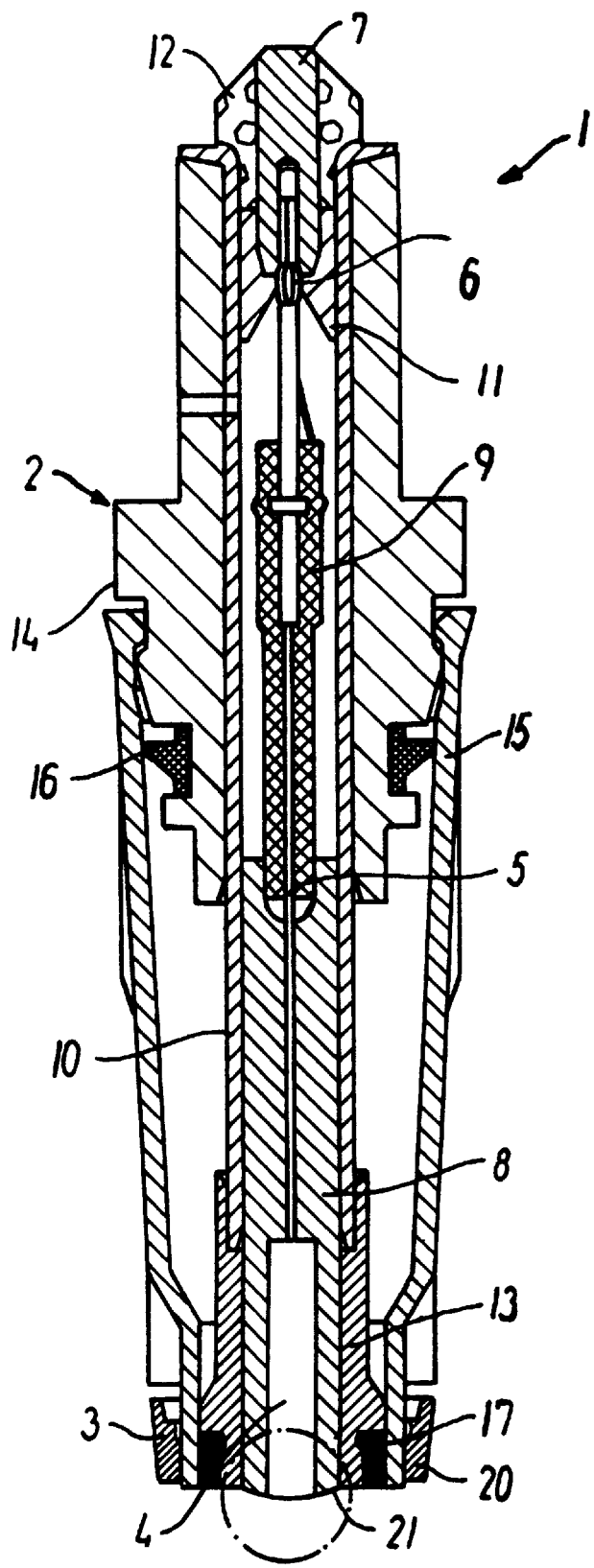
FIG. 1 is a sectional view of a sensor according to the invention.

The sensor of FIG. 1 is a sensor for measuring glucose. The measuring technique of the sensor is well-known. It is based on enzymatic conversion of glucose and oxygen into hydrogen peroxide ($H_2O_2$) and glyconic acid. Subsequently, the produced $H_2O_2$ is detected by an amperometric electrode. The sensor 1 is adapted to be placed in an analyzer for measurement of a blood sample such as the above-mentioned analyzer ABL™620 from Radiometer Medical A/S, Copenhagen, Denmark.

The sensor 1 primarily comprises an electrode 2 mounted on a membrane ring 3. The electrode 2 comprises a Pt anode 4 connected with a Pt wire 5 which is connected with anode contact 7 of silver through a micro plug 6. The Pt anode 4 and a part of the Pt wire 5 are glued into a glass part 8. Between the glass part 8 and the micro plug 6 the Pt wire 5 is protected by a tube 9 of heat shrink tubing. A tubular reference electrode 10 of silver surrounds the upper part of the glass part 8 and extends throughout the electrode 2's length to the anode contact 7 which is secured inside the reference electrode 10 by means of a fixation device 11 and epoxy 12. The lower part of the glass part 8 is surrounded by an electrode support 13 at which the membrane ring 3 is placed. The upper part of the reference electrode 10 is surrounded by a plug part 14, serving to mount the electrode 2 in a matching plug on an analyzer (not shown) and to securing a jacket 15. Between the electrode 2 and the jacket 15 are placed gaskets 16 and 17, ensuring that any electrolyte placed at the measuring surface of the electrode 2 does not evaporate from the sensor 1.

Figure 1A:
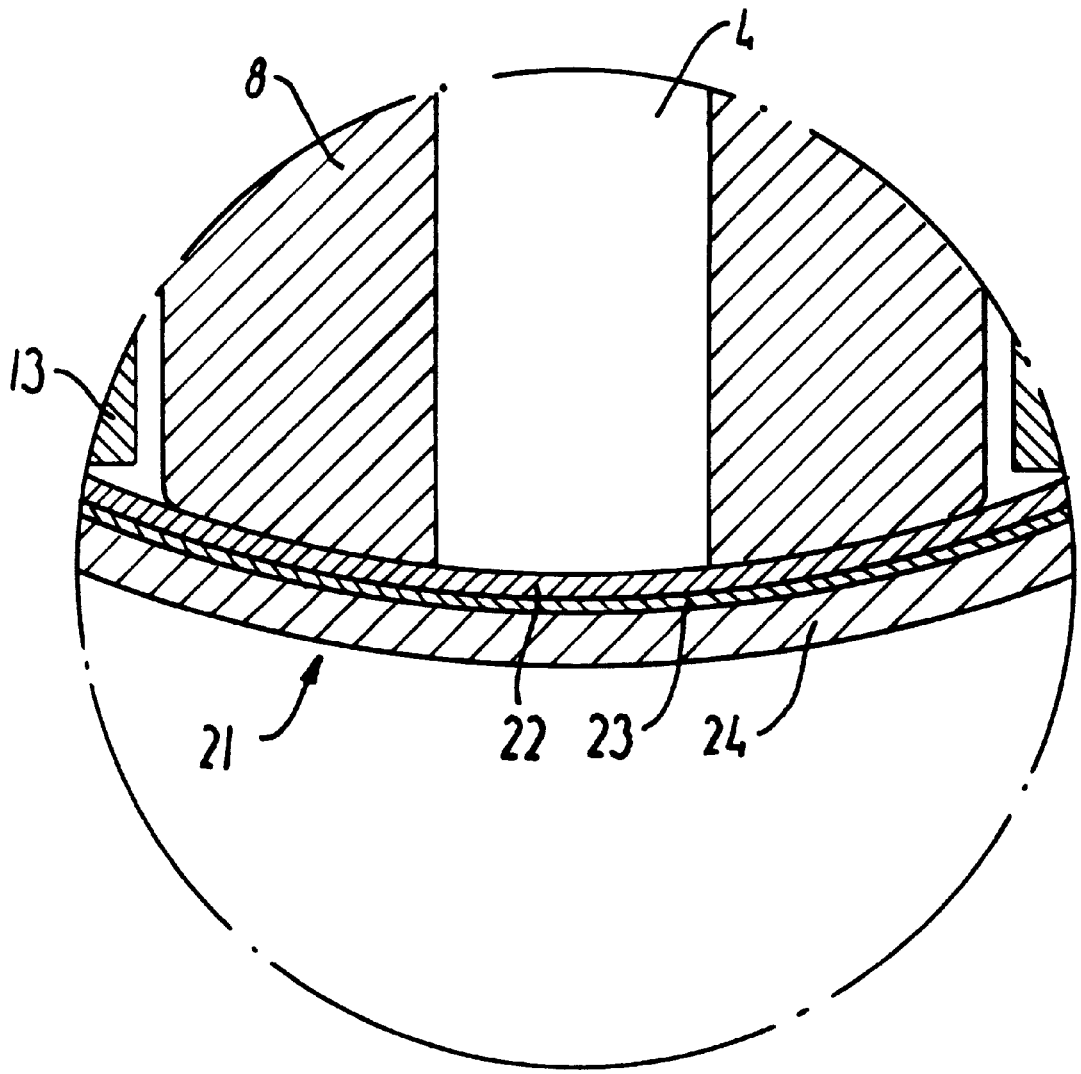
FIG. 1a is an enlarged section of FIG. 1.

The membrane ring 3, which is mounted at one end of the jacket 15, comprises a ring 20. A membrane 21 is kept in a stretched position above the lower opening of the ring 20. Said membrane 21, which is more clearly shown in FIG. 1a, consists of an approx. 6 μm porous membrane layer 22 of cellulose acetate (CA) onto which is applied an approx. 1 μm enzyme layer 23 of a cross-linked glucose oxidase (5 units per membrane) onto which is further applied an approx. 12 μm porous membrane layer 24 of polyethylene terepthalate (PETP). The membrane 21 is placed such that the CA membrane layer 22 faces the Pt anode 4 of the electrode 2 when the membrane ring 3 is mounted.

The PETP membrane layer 24 serves as a diffusion-limiting membrane. It ensures that the amount of glucose penetrating from the sample through the glucose oxidase layer 23, where the enzymatic conversion takes place, is not larger than sufficient oxygen for the conversion is available all the time. An example of how to prepare a PETP membrane layer is set forth below.

After the conversion in the glucose oxidase layer 23 the $H_2O_2$ formed penetrates through the CA membrane layer 22 to the Pt anode 4 where it is oxidized and thereby detected. The Pt anode 4 is polarized to +675 mV with an Ag/AgCl reference electrode.

The CA membrane layer 22 serves as an interference eliminating membrane as it is adapted to allow $H_2O_2$ to pass through, but not oxidable agents such as paracetamol, HEPES, and ascorbic acid which would otherwise interfere with the measuring result.

The CA membrane layer 22 with the applied glucose oxidase layer 23 is provided in a known manner, e.g. as disclosed in the specification of U.S. Pat. No. 3,979,274, The Yellow Springs Instrument Company, Inc.

Figure 2:
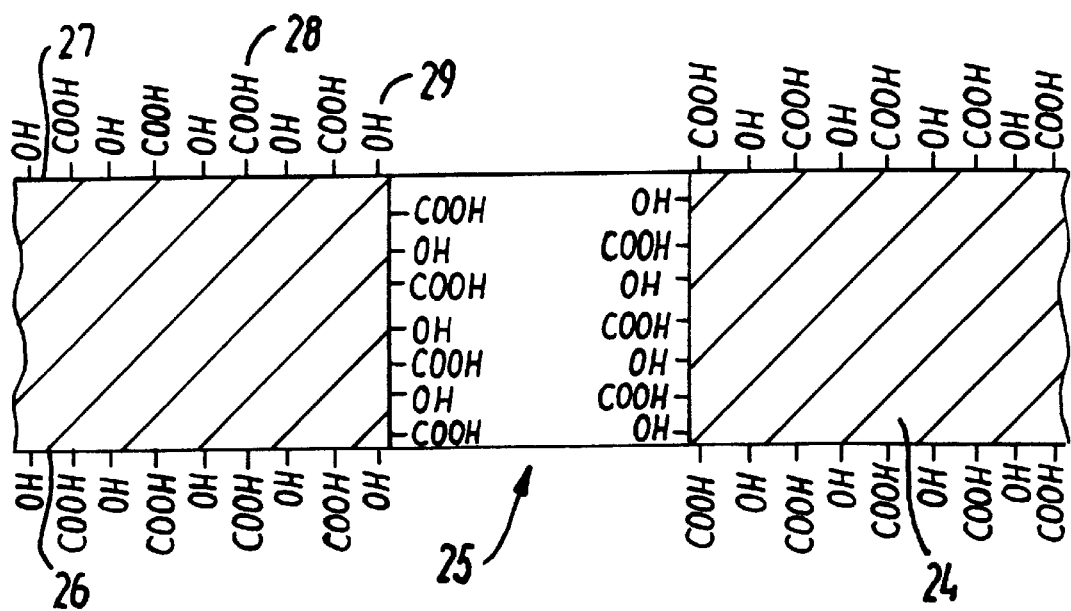
FIG. 2 is a schematic view of a section of an outer membrane for a sensor according to the invention prior to surface modification.

FIG. 2 shows a schematic view of a section of the PETP membrane layer 24 prior to its surface modification. The section is shown at one of the pores 25 of the membrane layer 24. For clarity, the section is somewhat distorted. As seen, the membrane layer 24 has free —COOH and —OH groups 28 and 29, respectively, on its surface. The groups are present on the outer surfaces 26, 27 of the membrane layer as well as on the surfaces of the pores 25.

Figure 3:
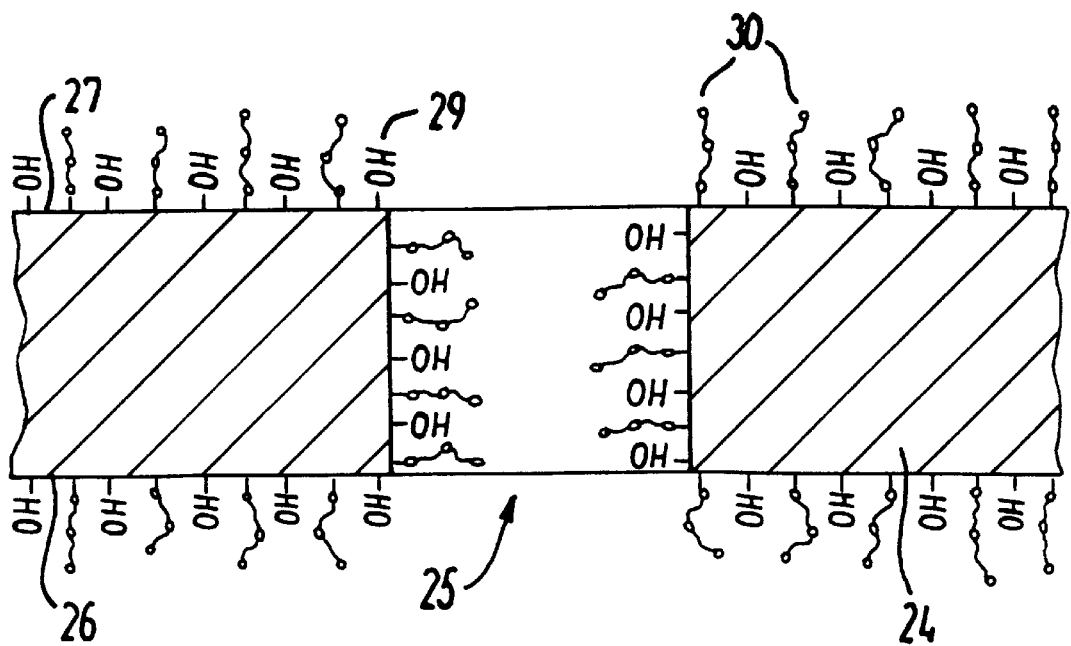
FIG. 3 is a schematic view of an outer membrane for a sensor according to the invention after surface modification.

FIG. 3 shows a schematic view corresponding to the one of FIG. 2, but showing the PETP membrane layer 24 after surface modification. As seen, chains 30 of polyethylene glycol are immobilised to the otherwise free —COOH groups (28 of FIG. 2) of the membrane layer. The lengths of the chains 30 are adapted so that they, when the measuring surface of the sensor 2 contacts the blood sample, are "dissolved" in the aqueous environment and by means of their "eelgrass"-like movements may prevent macromolecules, such as e.g. blood proteins, from getting into contact with and coating the surface of the membrane layer 24.

EXAMPLE 1

Preparation of a Modified PETP Membrane Layer for a Glucose Sensor

The PETP membrane layer is prepared from a biaxially stretched PETP foil (Mylar A from Whatman S. A., Louvain La-Neuve, Belgium) of the following specifications:

Thickness: 12 $\mu m \pm 1$ $\mu m$
Pore density: $1.6 \times 10^6$ pores/cm$^2$ (nominel)
Pore size: approx. 0.1 $\mu m$ (nominel)
Air flow: 1.6 mL/min/cm$^2$ at 0.7 Bar (10 psi)

PETP is selected as membrane material particularly on the basis of requirements to good resistance and strength. The PETP material is surface modified by a solution of a hydrophilic component of the following composition:

10 g PEG-200-(OH)$_2$
2 g CMC-MTS
0.2 g Triton CF-54
4000 ml demin. H$_2$O
pH 6.0–6.5 where

PEG-200-(OH)$_2$: Polyethylene glycol with two OH groups, mean molecular weight 200 g/mol, minimum content of tetraethylene glycol of 20% and of tri-, tetra- and pentaethylene glycol of 60%.

CMC-MTS: 1-Cyclohexyl-3-(2-morpholinoethyl) carbodiimide-metho-p-toluene sulphonate, 95% (coupling reagent)

The PETP material is cut into sheets and each sheet is secured to a frame. The frame with the PETP sheet is dipped into the reaction bath containing the hydrophilic component for approx. 18 hours at room temperature. Subsequently, the material is washed while stirred for approx. 15 minutes at room temperature with 0.1% Triton X-100 in demineralised water and washed twice while stirred in demineralised water, each time for approx. 10 minutes. Finally, the material is dried for at least 16 hours in a ventilated fume cupboard at room temperature. During this modification chains of PEG-200 are immobilised to the surface of the PETP material, including the pore surface, by means of ester binding to the free —COOH groups on the surface.

The surface modified PETP material is cut in the shape of wafers which are collected with the previously prepared CA/glucose oxidase membrane layers 22, 23. The membrane 21 is now ready for further mounting into the membrane ring 3.

A membrane prepared by means of the above-mentioned procedure has shown particularly good durability—it is durable for at least 30 days when placed in an operating analyzer.

The PEG-200 chains on the membrane surface serve as a hydrogel, thus making the surface non-sticky; at the same time being polar and non-reactive, thus eliminating the capability of i.a. the blood proteins to form deposits onto the surface.

EXAMPLE 2

Selection of a Hydrophilic Component

During the process of finding a PEG providing the best modified membrane as to stable measurements, PETP membranes modified with different types of polyethylene glycol (PEG) (primarily of different molecular weights) and by slightly different procedures were prepared. Measurement results from 10 measurements using each of said membranes on samples of whole blood were compared with each other and with measurement results from an unmodified membrane and a membrane washed in MeOH. The results appear from Table 1 below.

TABLE 1

| Modification | Decrease during 10 blood measurements % |
|---|---|
| Unmodified PETP membrane | 30 |
| PETP membrane wased in MeOH | 7 |
| PEG-5000-NH2 in THF/DCC | 7.2 |
| PEG-4000-(COOH)$_2$ | 8.3 |
| PEG-2000-(COOH)$_2$ | 4.0 |
| PEG-200-(OH)$_2$, CMC-MTS, aqueous | 1.8 |
| PEG-200-(OH)$_2$, without coupling reagent, aqueous | 5.2 |
| PEG-200-OMe, CMC-MTS, aqueous | 4.7 |

As seen from the table, it is clear that the PETP membrane modified with PEG-200-(OH)$_2$ according to the above procedure produced the absolutely best result. The more hydrophobic PEG-200-OMe, with only one OH group, showed a stronger tendency towards coating of the membrane surface. Further, there seems to be a tendency towards a larger decrease of the measurement results with a larger molecular weight of PEG.

No experiments have been performed with PEG having molecular weights in the range of 200 g/mol and 2000 g/mol, but it is assessed that PEG with molecular weights slightly above 200 g/mol, perhaps up to 1000 g/mol, will be suitable for modification of the PETP membrane. Further, it is assessed that also PEG with molecular weights of less than 200 g/mol, e.g. 100 g/mol, will be suitable.

What is claimed is:

1. A sensor for measuring an analyte in a biological sample comprising a measuring surface having an associated membrane, said membrane comprising a modified membrane surface facing the sample through which the analyte to be measured permeates toward the measuring surface, said membrane surface having free groups prior to surface modification, wherein the surface is modified by immobilizing a hydrophilic component on the surface in such a manner that chains of the hydrophilic component are chemically bonded to the free groups on the surface forming said modified membrane surface, thus providing said modified membrane surface with a more hydrophilic character relative to its unmodified state.

2. The sensor according to claim 1, wherein said membrane has pores extending from the first surface of said membrane to the opposite surface of said membrane.

3. The sensor according to claim 2, wherein chains of the hydrophilic component have penetrated into the pores of the modified membrane and are bonded to free groups on the surface of the pores.

4. The sensor according to claim 1, wherein said membrane is a multi-layered membrane and wherein the layer which faces the sample has pores which extend from the first surface of the layer to the opposite surface of the layer.

5. The sensor according to claim 4, wherein chains of the hydrophilic component have penetrated into the pores of said modified membrane and are bonded to free groups on the surface of the pores.

6. The sensor according to claim 4, wherein said membrane surface facing the sample comprises polyethylene terephtalate.

7. The sensor according to claim 1, wherein said hydrophilic component is polyethylene glycol.

8. The sensor according to claim 7, wherein chains of polyethylene glycol are bonded to free —COOH groups of said membrane surface.

9. The sensor according to claim 1 wherein the chemical bond is an amide bond.

10. The sensor according to claim 1 wherein the chemical bond is an ester bond.

11. The sensor according to claim 1 wherein the hydrophilic component has at least two hydrophilic groups.

12. The sensor according to claim 11 where the hydrophilic component has two hydrophilic groups.

13. The membrane for use in a sensor comprising a modified membrane surface having free groups prior to surface modification, wherein the surface is modified by immobilizing a hydrophilic component on the surface in such a manner that chains of the hydrophilic component are chemically bonded to the free groups on the surface forming the modified membrane surface, thus providing the modified membrane surface with a more hydrophilic character relative to its unmodified state.

14. The membrane according to claim 13 wherein the membrane has pores extending from the first surface of the membrane to the opposite surface of the membrane.

15. The membrane according to claim 13 wherein the membrane is a multi-layered membrane and wherein the layer which faces the sample has pores which extend from the first surface of the layer to the opposite surface of the layer.

16. The membrane according to claim 14 wherein chains of the hydrophilic component have penetrated into the pores of the modified membrane and are bonded to free groups on the surface of the pores.

17. The membrane according to claim 15 wherein chains of the hydrophilic component have penetrated into the pores of the modified membrane and are bonded to free groups on the surface of the pores.

18. The membrane according to claim 13 wherein the modified membrane comprises polyethylene terephtalate.

19. The membrane according to claim 13 wherein the hydrophilic component is polyethylene glycol.

20. The membrane according to claim 13 wherein chains of polyethylene glycol are bonded to free COOH groups of the membrane surface.

21. The membrane according to claim 13 wherein the membrane is kept in a stretched position by a primarily circular membrane ring.

22. The membrane according to claim 13 wherein the membrane ring is connected with a jacket adapted to be mounted on an electrode.

23. The membrane according to claim 13 wherein the chemical bond is an amide bond.

24. The membrane according to claim 13 wherein the chemical bond is an ester bond.

25. The membrane according to claim 13 wherein the hydrophilic component has at least two hydrophilic groups.

26. The membrane according to claim 25 wherein the hydrophilic component has two hydrophilic groups.

* * * * *